(12) United States Patent
Subramaniyam

(10) Patent No.: US 9,217,107 B2
(45) Date of Patent: Dec. 22, 2015

(54) AMINE BASED ADDITIVE COMPOSITION FOR CONTROL AND INHIBITION OF POLYMERIZATION OF AROMATIC VINYL MONOMERS, AND METHOD OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 14/366,223

(22) PCT Filed: Dec. 21, 2012

(86) PCT No.: PCT/IN2012/000839
§ 371 (c)(1),
(2) Date: Jun. 17, 2014

(87) PCT Pub. No.: WO2013/102930
PCT Pub. Date: Jul. 11, 2013

(65) Prior Publication Data
US 2014/0364662 A1    Dec. 11, 2014

(30) Foreign Application Priority Data

Dec. 26, 2011 (IN) .................. 3653/MUM/2011

(51) Int. Cl.
*C07C 7/20*         (2006.01)
*C09K 15/30*        (2006.01)
*C07B 63/04*        (2006.01)

(52) U.S. Cl.
CPC .............. *C09K 15/30* (2013.01); *C07B 63/04* (2013.01); *C07C 7/20* (2013.01)

(58) Field of Classification Search
CPC ........................................................ C07C 7/20
USPC ..................................... 585/5, 952; 203/8, 9
See application file for complete search history.

(56) References Cited

U.S. PATENT DOCUMENTS

| 4,105,506 | A  | * | 8/1978  | Watson ........................ 203/9 |
| 4,466,905 | A  | * | 8/1984  | Butler et al. .................. 585/5 |
| 5,290,888 | A  | * | 3/1994  | Gatechair et al. ............. 526/83 |
| 6,403,850 | B1 | * | 6/2002  | Benage et al. ................. 585/5 |
| 6,673,879 | B2 | * | 1/2004  | Shahid .......................... 526/82 |
| 7,128,826 | B2 | * | 10/2006 | Eldin et al. ............... 208/48 AA |
| 7,553,896 | B2 | * | 6/2009  | Ma et al. ..................... 524/186 |
| 7,651,635 | B1 | * | 1/2010  | Lewis .......................... 252/403 |
| 8,128,804 | B2 | * | 3/2012  | Weyler et al. ............ 208/48 AA |
| 8,246,858 | B2 | * | 8/2012  | Nakajima et al. .......... 252/405 |
| 8,809,431 | B2 | * | 8/2014  | Weyler et al. ............... 524/320 |
| 2004/0034247 | A1 |   | 2/2004  | Eldin |
| 2013/0072729 | A1 | * | 3/2013  | Link et al. ...................... 585/4 |
| 2014/0350313 | A1 | * | 11/2014 | Subramaniyam ............... 585/5 |

FOREIGN PATENT DOCUMENTS

| IN | 3653MUM2011     | 12/2011 |
| WO | 2013054353 A1   | 4/2013  |
| WO | 2013102930 A1   | 7/2013  |
| WO | 2013102930 A8   | 7/2013  |

OTHER PUBLICATIONS

Foreign communication from the priority application—International Search Report and Written Opinion, PCT/IN2012/000839, Mar. 6, 2013, 9 pages.

* cited by examiner

*Primary Examiner* — Ellen McAvoy
(74) *Attorney, Agent, or Firm* — Conley Rose, P.C.; Rodney B. Carroll

(57) ABSTRACT

The present invention relates to an improved amine based additive composition for control and inhibition of polymerization of aromatic vinyl monomers including styrene comprising one or more of the quinone methide or derivatives thereof, one or more of nitroxide compounds and further comprising one or more of aliphatic tertiary amines. In one embodiment, the present invention also relates to method of use of presently provided composition. In another embodiment, the present invention also relates to method of controlling and inhibiting polymerization of aromatic vinyl monomers, particularly of styrene by employing presently provided composition. In still another embodiment, the present invention also relates to method of preparation of presently provided composition.

25 Claims, No Drawings

AMINE BASED ADDITIVE COMPOSITION FOR CONTROL AND INHIBITION OF POLYMERIZATION OF AROMATIC VINYL MONOMERS, AND METHOD OF USE THEREOF

CROSS-REFERENCE TO RELATED APPLICATIONS

This application is a filing under 35 U.S.C. 371 of International Application No. PCT/IN2012/000839 filed Dec. 21, 2012, entitled "Improved Amine Based Additive Composition for Control and Inhibition of Polymerization of Aromatic Vinyl Monomers, and Method of Use Thereof," which claims priority to Indian Patent Application No. 3653/MUM/2011 filed Dec. 26, 2011, which applications are incorporated by reference herein in their entirety.

FIELD OF THE INVENTION

The present invention relates to an improved amine based additive composition for control and inhibition of polymerization of aromatic vinyl monomers, wherein aromatic vinyl monomer includes styrene, wherein improvement comprises a composition of one or more tertiary amines with mixture of one or more of aromatic compounds and one or more nitroxide (or nitroxyl) compounds.

In one embodiment, the present invention relates to use of improved amine based additive composition of present invention to control and inhibit polymerization of aromatic vinyl monomers including styrene, wherein improvement comprises use of a composition comprising one or more tertiary amines with mixture of one or more of aromatic compounds and one or more nitroxide (or nitroxyl) compounds.

In another embodiment, the present invention relates to method of preparation of improved additive composition of present invention for control and inhibition of polymerization of aromatic vinyl monomers including styrene, wherein improvement comprises preparation of composition comprising one or more tertiary amines with mixture of one or more of aromatic compounds and one or more nitroxide (or nitroxyl) compounds.

In still another embodiment, the present invention relates to method of controlling and inhibiting polymerization of aromatic vinyl monomers including styrene by employing improved additive composition of present invention, wherein improvement comprises treating the stream containing aromatic vinyl monomers with a composition comprising one or more tertiary amines with mixture of one or more of aromatic compounds and one or more nitroxide (or nitroxyl) compounds.

BACKGROUND OF THE INVENTION

The polymerization of aromatic vinyl monomers including styrene during processing is a matter of concern, because it causes formation of unwanted polymers and results in loss of yield of end product and makes the process un-economical.

In the art use of inhibitors and retarders, and combination thereof to overcome problem of polymerization of styrene has been reported.

The problem of using the inhibitors alone is that these are to be added continuously or at regular interval, because once they are consumed, the polymerization will re-start.

The problem of using the retarders alone is that these are not very effective to reduce polymerization of styrene to a level of substantial inhibition or to the acceptable level of inhibition.

The prior art proposes quinone methide based composition comprising quinone methide and 4HT (4 hydroxy tempo 2,2,6,6-tetramethyl-,1-oxide) as styrene polymerization inhibitor. However, the inventor has found [refer to examples and corresponding data] that main problem of using this known composition of quinone methide (QM) and 4HT is that even with higher amounts of the composition, the problem of polymerization is not resolved to acceptable level.

Therefore, the industry is aiming for additive composition wherein the amount of aromatic and nitroxide compounds can be reduced or minimized so that the resulted composition is economical as well as safe for human being.

Any effort to reduce or minimize consumption of aromatic compounds and/or nitroxide compounds will lessen the problems of the industry.

NEED OF THE INVENTION

Therefore, there is still a need of an effective additive composition and method of its use and preparation, and method of controlling and inhibiting polymerization of vinyl aromatic monomers including styrene by employing said composition, wherein the additive composition is not only suitable for substantial control and inhibition of polymerization of aromatic vinyl monomers including styrene, but also comprises substantially reduced or minimized amounts of aromatic and nitroxide compounds.

SUMMARY OF THE INVENTION

Therefore, the present invention aims at providing a solution to above-described existing industrial problems by providing effective additive composition and method of its use and preparation, and method of controlling and inhibiting polymerization of vinyl aromatic monomers including styrene, wherein the additive composition is not only suitable for substantial control and inhibition of polymerization of aromatic vinyl monomers including styrene, but also comprises substantially reduced or minimized amounts of aromatic and nitroxide compounds.

OBJECTS OF THE INVENTION

Accordingly, the main object of present invention is to provide an effective and improved amine based additive composition and method of its use and preparation, and method of controlling and inhibiting polymerization of vinyl aromatic monomers, wherein the additive composition is not only suitable for substantial control and inhibition of polymerization of aromatic vinyl monomers including styrene, but also comprises substantially reduced or minimized amounts of aromatic and nitroxide compounds.

Another main object of present invention is to provide an effective and improved amine based additive composition and method of its use and preparation, and method of controlling and inhibiting polymerization of vinyl aromatic monomers, wherein the additive composition comprises substantially reduced or minimized amount of aromatic and nitroxide compounds, and is still suitable for substantial control and inhibition of polymerization of aromatic vinyl monomers including styrene, and is still required in relatively lower dosage as compared to dosage of combination of aromatic and nitroxide compounds for achieving the same or better acceptable level of control and inhibition of polymerization of styrene.

This is also an object of present invention to provide an effective and improved amine based additive composition and method of its use and preparation, and method of controlling and inhibiting polymerization of vinyl aromatic monomers, wherein the additive composition comprises one or more of amines, and reduced or minimized amount of one or more of aromatic and one or more of nitroxide compounds, and is still suitable for substantial control and inhibition of polymerization of aromatic vinyl monomers including styrene, and is still required in relatively lower dosage as compared to dosage of combination of aromatic and nitroxides compounds for achieving the same or better acceptable level of control and inhibition of polymerization of styrene, and wherein the amine is one or more of tertiary amines.

The present invention particularly aims at providing an effective and improved amine based additive composition and method of its use and preparation, and method of controlling and inhibiting polymerization of vinyl aromatic monomers, wherein the additive composition comprises one or more of amines, and reduced or minimized amounts of one or more of aromatic compounds including quinone methide (QM) and one or more of nitroxides (i.e. nitroxyl) compounds including 1 oxyl-2,2,6,6, tetramethylpiperidin-4-ol (or 4 Hydroxy Tempo or 4HT) and is still suitable for substantial control and inhibition of polymerization of aromatic vinyl monomers including styrene, and is still required in relatively lower dosage as compared to dosage of combination of aromatic and nitroxides compounds for achieving the same or better acceptable level of control and inhibition of polymerization of styrene, and wherein the amine is one or more of tertiary amines, and therefore, the composition of present invention is not only economical, but is also environment friendly.

The present invention aims at improving the performance of additive compositions comprising mixture of aromatic compounds and nitroxide compounds, wherein the present composition comprises one or more of aromatic compounds and one or more of nitroxide compounds, and further comprises one or more of tertiary amines.

The present invention aims at improving the performance of additive compositions comprising mixture of aromatic compounds and nitroxide compounds at a wider range of temperature including the higher temperature, wherein the composition comprises one or more of aromatic compounds and one or more of nitroxide compounds, and further comprises one or more of tertiary amines.

The present invention aims at improving the performance of additive compositions comprising mixture of aromatic compounds and nitroxide compounds at a wider range of temperature including the higher temperature and in presence of air, wherein the composition comprises one or more of aromatic compounds and one or more of nitroxide compounds, and further comprises one or more of tertiary amines.

Other objects and advantages of present invention will become more apparent from the following description when read in conjunction with examples, which are not intended to limit scope of present invention.

DETAILED DESCRIPTION OF THE INVENTION

With aim to overcome above-described problems of prior art and to achieve above-described objects of the present invention, the inventor has found that when one or more of tertiary amines is added to composition comprising one or more of aromatic and one or more of nitroxide compounds, then not only polymerization controlling and inhibiting efficiency of composition comprising aromatic and nitroxide compounds is substantially improved, but polymerization of aromatic vinyl monomers including styrene, surprisingly and unexpectedly, is also controlled and inhibited to the acceptable level with substantially reduced and minimized dosage of aromatic and nitroxide compounds in a composition comprising one or more of tertiary amines, and one or more of aromatic compounds and one or more of nitorxide compounds, which makes the present composition economical as well as environment friendly.

With aim to overcome above-described problems of prior art and to achieve above-described objects of the present invention, the inventor has found that when one or more of tertiary amines selected from a group consisting of hydroxyl alkyl tertiary amine and oxide treated amine, preferably aliphatic tertiary amine containing one or more hydroxyl groups is added to composition comprising one or more of aromatic compounds, preferably quinone methide (QM) and one or more of nitroxide compounds, then not only polymerization controlling and inhibiting efficiency of composition comprising aromatic and nitroxide compounds is substantially improved, but polymerization of aromatic vinyl monomers including styrene, surprisingly and unexpectedly, is also controlled and inhibited to the acceptable level with substantially reduced and minimized dosage of aromatic and nitroxide compounds in a composition comprising one or more of aromatic compounds and one or more of nitorxide compounds, and further comprising one or more of tertiary amines selected from a group consisting of hydroxyl alkyl tertiary amine, and oxide treated amine, preferably aliphatic tertiary amines containing one or more hydroxyl groups, which makes the present composition economical as well as environment friendly.

Accordingly, the present invention relates to an improved amine based additive composition for controlling and inhibition of polymerization of aromatic vinyl monomers including styrene comprising:

(A) one or more of the quinone methide or derivatives thereof, (B) one or more of nitroxides (i.e. nitroxyl) compounds, and characterized in that the said composition further comprises:

(C) one or more of aliphatic tertiary amines or mixture thereof.

In accordance with present invention, the aliphatic amine is an aliphatic tertiary amine, which contains one or more hydroxyl groups in the alkyl chain of the tertiary amine, preferably contains three or four hydroxyl groups in the alkyl chain of the tertiary amine.

In accordance with present invention, in the aliphatic tertiary amine containing one or more hydroxyl groups, the hydroxyl groups are hydroxyalkyl groups.

In accordance with present invention, the hydrocarbon in the aliphatic tertiary amine may be linear, branched or cyclic.

In accordance with present invention, the hydrocarbon in the aliphatic tertiary amine may contain one or more hydroxy alkyl groups.

In accordance with most preferred embodiment of the present invention, the aliphatic tertiary amine containing three hydroxyl groups is tri-isopropanol amine or tris(2-hydroxypropyl)amine [TIPA].

In accordance with one of the preferred embodiments of the present invention, the aliphatic tertiary amine containing hydroxyl groups is N,N,N',N'-Tetrakis(2-hydroxyethyl)ethylene-diamine) (THEED).

In accordance with another preferred embodiment of the present invention, the aliphatic tertiary amine containing hydroxyl groups is N,N,N',N'-Tetrakis(2-hydroxypropyl)ethylene-diamine) (Quadrol®).

In accordance with another preferred embodiment of the present invention, the composition of the present invention may comprise one or more of above-said aliphatic tertiary amines containing hydroxyl groups or mixture thereof.

Therefore, in one embodiment, the present invention relates to an improved amine based additive composition for control and inhibition of polymerization of aromatic vinyl monomers including styrene comprising:

(A) one or more of the quinone methide or derivatives thereof, (B) one or more of nitroxides (i.e. nitroxyl) compounds, and characterized in that the said composition further comprises:

(C) one or more of tertiary amines, wherein said tertiary amine is selected from a group consisting of:
- i) hydroxyl alkyl tertiary amine which is tris(2-hydroxypropyl)amine (TIPA);
- ii) propylene oxide treated amine which is N,N,N',N'-Tetrakis(2-hydroxypropyl)ethylene-diamine) (Quadrol®); and
- iii) ethylene oxide treated amine which is N,N,N',N'-Tetrakis(2-hydroxyethyl)ethylene-diamine) (THEED); or
- iv) mixture thereof.

The inventor has been found that when composition of present invention comprises one or more of said tertiary amines, the efficiency of aromatic and nitroxide compounds to control and inhibit polymerization of aromatic vinyl monomers including styrene is, surprisingly and unexpectedly, substantially improved to the acceptable level that's too at substantially reduced or minimized dosages of aromatic and nitroxide compounds, thereby making the composition of present invention relatively more economical and environment friendly.

In accordance with one of the embodiments of the present invention, the composition of present invention comprises:
- a) about 40 to about 99.9% by weight of I) mixture of one or more of said quinone methide or derivatives thereof (herein after may be referred to QM) and one or more of said nitroxides (i.e. nitroxyl) compounds; and
- b) about 0.1 to about 60% by weight of II) one or more of said tertiary amines or mixture thereof.

In accordance with one of the embodiments of the present invention, the said quinone methide or derivatives thereof includes benzyl quinone methide, preferably 4-benzylidene, 2,6-di-tert-butyl cyclohexa-2,5-dienone.

It may be noted that 'said quinone methide or derivatives thereof' herein after may be referred to as QM.

In accordance with one of the embodiments of the present invention, the said nitroxides (i.e. nitroxyl) compounds include 1 oxyl-2,2,6,6, tetramethylpiperidin-4-ol or 4-hydroxy-2,2,6,6-tetramethylpiperidin-1-oxyl (or 4 Hydroxy Tempo or 4HT).

It may be noted that 'said nitroxides (i.e. nitroxyl) compounds including 1 oxyl-2,2,6,6, tetramethylpiperidin-4-ol (or 4 Hydroxy Tempo or 4HT) herein after may be referred to as 4HT.

In accordance with one of the embodiments of the present invention, in the mixture of QM and 4HT, the QM is taken in an amount varying from about 0.5 to about 99.5% by wt and 4HT is taken in an amount varying from about 99.5 to about 0.5% by wt. of the mixture.

In accordance with the present invention, the mixture of QM and 4HT comprises QM and 4HT in a weight ratio varying from about 99.5:0.5 to 0.5:99.5, preferably from about 95:5 to 5:95, more preferably from about 90:10 to about 10:90.

In accordance with the present invention, the said tertiary amine or mixture thereof is taken an amount varying from about 0.01 to about 60% by wt of the composition.

In accordance with another preferred embodiment of the present invention, the present composition does not comprise:
- i) triethanolamine (TEA);
- ii) Tris[N-butylamine] (TBA);
- iii) monoethanolamine (MEA);
- iv) dibutyl amine (DBA);
- v) diethanol amine (DEA);
- vi) dipropyl amine (DPA);
- vii) ethylene diamine (EDA); and
- viii) tetraethylenepentamine (TEPA), and
- ix) mixture thereof.

It may be noted that the stream comprising aromatic vinyl monomers including styrene may be referred to as monomer stream or as aromatic vinyl monomers stream.

In accordance with one of the preferred embodiments of the present invention, the composition of present invention is added to the stream containing aromatic vinyl monomers including styrene in an amount varying from about 0.01 ppm to about 2000 ppm, preferably from about 1 ppm to about 2000 ppm by weight of the stream of the monomers including styrene.

Accordingly, in another embodiment, the present invention also relates to method of using said improved amine based additive composition of present invention described herein, a reference to which is drawn in entirety, to control and inhibit polymerization of aromatic vinyl monomers including styrene, wherein the stream comprising aromatic vinyl monomer including styrene is treated with an additive composition comprising:

(A) one or more of said quinone methide or derivatives thereof, (B) one or more of said nitroxides (i.e. nitroxyl) compounds, and characterized in that the said composition further comprises:

(C) one or more of said aliphatic tertiary amines or mixture thereof.

In particular, in second embodiment, the present invention relates to a method of using said additive composition of the present invention described herein, a reference to which is drawn in entirety, for controlling and inhibition of polymerization of aromatic vinyl monomers including styrene, wherein the stream comprising aromatic vinyl monomer including styrene is treated with the additive composition comprising:

(A) one or more of the quinone methide or derivatives thereof, (B) one or more of nitroxides (i.e. nitroxyl) compounds, and characterized in that the said composition further comprises:

(C) one or more of tertiary amines, wherein said tertiary amine is selected from a group consisting of:
- i) hydroxyl alkyl tertiary amine which is tris(2-hydroxypropyl)amine (TIPA);
- ii) propylene oxide treated amine which is N,N,N',N'-Tetrakis(2-hydroxypropyl)ethylene-diamine) (Quadrol®); and iii) ethylene oxide treated amine which is N,N,N',N'-Tetrakis(2-hydroxyethyl)ethylene-diamine) (THEED); or iv) mixture thereof.

It may be noted that the stream comprising aromatic vinyl monomers including styrene may be referred to as monomer stream or as aromatic vinyl monomers stream.

In accordance with one of the embodiments of the present invention, the method of using said additive composition of the present invention comprises treating said stream comprising aromatic vinyl monomers including styrene with about 0.01 ppm to about 2000 ppm, preferably from about 1 ppm to about 2000 ppm of said additive composition based on weight of the monomers.

In accordance with one of the preferred embodiments of the present invention, one or more of the said quinone methide or derivatives thereof, one or more of the said nitroxides (i.e. nitroxyl) compounds, and one or more of the said tertiary amines are added to the monomers stream either individually or after mixing.

It may be noted that all the features of the composition of the present invention described herein, a reference to which is drawn in entirety, are deemed to have been included in present method of using said additive composition of the present invention.

Accordingly, in third embodiment, the present invention also relates to method for controlling and inhibiting polymerization of aromatic vinyl monomers including styrene by adding said amine based additive composition of present invention described herein, a reference to which is drawn in entirety, to the stream comprising aromatic vinyl monomers including styrene, wherein the additive composition comprises:

(A) one or more of said quinone methide or derivatives thereof, (B) one or more of said nitroxides (i.e. nitroxyl) compounds, and characterized in that the said composition further comprises:

(C) one or more of said aliphatic tertiary amines or mixture thereof.

In particular, in third embodiment, the present invention relates to a method for controlling and inhibition of polymerization of aromatic vinyl monomers including styrene by adding said additive composition of the present invention described herein, a reference to which is drawn in entirety, to the monomers stream, wherein said composition comprises:

(A) one or more of the quinone methide or derivatives thereof, (B) one or more of nitroxides (i.e. nitroxyl) compounds, and characterized in that the said composition further comprises:

(C) one or more of tertiary amines, wherein said tertiary amine is selected from a group consisting of:

i) hydroxyl alkyl tertiary amine which is tris(2-hydroxypropyl)amine (TIPA);

ii) propylene oxide treated amine which is N,N,N',N'-Tetrakis(2-hydroxypropyl)ethylene-diamine) (Quadrol®); and iii) ethylene oxide treated amine which is N,N,N',N'-Tetrakis(2-hydroxyethyl)ethylene-diamine) (THEED); or iv) mixture thereof.

It may be noted that the stream comprising aromatic vinyl monomers including styrene may be referred to as monomer stream or as aromatic vinyl monomers stream.

In accordance with one of the preferred embodiments of the present invention, the method for controlling and inhibition of polymerization of aromatic vinyl monomers including styrene by employing said additive composition of the present invention comprises adding an amount varying from about 0.01 ppm to about 2000 ppm, preferably from about 1 ppm to about 2000 ppm of the said composition to the aromatic vinyl monomers stream including styrene based on weight of the monomers.

In accordance with one of the preferred embodiments of the present invention, one or more of the said quinone methide or derivatives thereof, one or more of the said nitroxides (i.e. nitroxyl) compounds, and one or more of the said tertiary amines are added to the monomers stream either individually or after mixing.

It may be noted that all the features of the composition of the present invention described herein, a reference to which is drawn in entirety, are deemed to have been included in present method for controlling and inhibition of polymerization of aromatic vinyl monomers including styrene by employing said additive composition of the present invention.

In accordance with one of the embodiments of the present invention, the composition of present invention may be mixed with stream containing aromatic vinyl monomers either before the stream enters into processing system or after the stream has entered into processing system, but preferably the composition is added to the stream containing aromatic vinyl monomers before its processing starts so that polymerization of aromatic vinyl monomers is avoided or minimized.

In accordance with one of the embodiments of the present invention, the present composition may be used over a wide range of temperature varying from about 50 degree C. to about 180 degree C., preferably from about 60 degree C. to about 180 degree C.

The composition of present invention may be prepared in any known manner to prepare the compositions.

Accordingly, in fourth embodiment, the present invention also relates to method of preparing said amine based additive composition of present invention described herein, a reference to which is drawn in entirety, for controlling and inhibiting polymerization of aromatic vinyl monomers including styrene, wherein one or more of said aromatic compounds, one or more of said nitroxide compounds are mixed with one or more of said amine compounds either individually or after mixing.

In particular, in fourth embodiment, the present invention relates to a method for preparation of additive composition of the present invention described herein, a reference to which is drawn in entirety, for controlling and inhibition of polymerization of aromatic vinyl monomers including styrene, wherein said method comprises:

step of mixing (A) one or more of quinone methide or derivatives thereof, and (B) one or more of nitroxides (i.e. nitroxyl) compounds, and characterized in that said quinone methide or derivatives thereof and said nitroxides (i.e. nitroxyl) compounds or mixture thereof is further mixed with (C) one or more of tertiary amines, wherein said tertiary amine is selected from a group consisting of:

i) hydroxyl alkyl tertiary amine which is tris(2-hydroxypropyl)amine (TIPA);

ii) propylene oxide treated amine which is N,N,N',N'-Tetrakis(2-hydroxypropyl)ethylene-diamine) (Quadrol®); and iii) ethylene oxide treated amine which is N,N,N',N'-Tetrakis(2-hydroxyethyl)ethylene-diamine) (THEED); or
iv) mixture thereof.

In accordance with one of the embodiments of the present invention, the method for preparation of additive composition of the present invention comprises mixing one or more of the tertiary amines with one or more of the quinone methide or derivatives thereof and one or more of nitroxides (i.e. nitroxyl) compounds either individually or after mixing.

In accordance with one of the embodiments of the present invention, the composition prepared may be used over a range of temperature varying from about 50 degree C. to about 180 degree C., preferably from about 60 degree C. to about 180 degree C.

It may be noted that the stream comprising aromatic vinyl monomers including styrene may be referred to as monomers stream or as aromatic vinyl monomers stream.

It may also be noted that all the features of the composition of the present invention described herein, a reference to which is drawn in entirety, are deemed to have been included in present method for preparation of additive composition of the present invention.

In one of the embodiments, the inventor has found that when present composition comprises any one of the tertiary amines selected from a group consisting of N,N,N',N'-Tetrakis(2-hydroxyethyl)ethylene-diamine) (THEED) and N,N,N',N'-Tetrakis(2-hydroxypropyl)ethylene-diamine) (Quadrol®), then efficiency for controlling and inhibition of polymerization of aromatic vinyl monomers including styrene of the mixture comprising quinone methide or derivatives thereof and nitroxides (i.e. nitroxyl) compounds is substantially improved, however, the improvement is not as substantial as for the composition comprising tris(2-hydroxypropyl)amine (TIPA). Therefore, as per most preferred embodiment of the present invention, tris(2-hydroxypropyl)amine (TIPA) is most preferred amine, and as per more preferred embodiment of the present invention, N,N,N',N'-Tetrakis(2-hydroxyethyl)ethylene-diamine) (THEED) and N,N,N',N'-Tetrakis(2-hydroxypropyl)ethylene-diamine) (Quadrol®) are the more preferred amines of the present invention.

In another embodiment, the inventor has found that when the present composition comprises any one of the amines selected from a group consisting of:
i) triethanolamine (TEA);
ii) Tris[N-butylamine] (TBA);
iii) monoethanolamine (MEA);
iv) dibutyl amine (DBA);
v) diethanol amine (DEA);
vi) dipropyl amine (DPA);
vii) ethylene diamine (EDA); and
viii) tetraethylenepentamine (TEPA), and
ix) mixture thereof.

then efficiency for controlling and inhibition of polymerization of aromatic vinyl monomers including styrene of the aromatic nitro compounds is, surprisingly and unexpectedly, substantially reduced. Therefore, in one embodiment, the present composition does not comprise any one of the amines selected from a group consisting of:
i) triethanolamine (TEA);
ii) Tris[N-butylamine] (TBA);
iii) monoethanolamine (MEA);
iv) dibutyl amine (DBA);
v) diethanol amine (DEA);
vi) dipropyl amine (DPA);
vii) ethylene diamine (EDA); and
viii) tetraethylenepentamine (TEPA), and
ix) mixture thereof.

It may be noted that some of these amines result in very marginal improvement in efficiency of mixture comprising quinone methide or derivatives thereof and nitroxides (i.e. nitroxyl) compounds, but same is not commercially viable.

Examples

Further advantages and embodiments of the present invention will become more apparent from the following examples.

The present invention is now described with the help of following examples, which are not intended to limit scope of the present invention, but have been incorporated to illustrate mode and best mode of performing the present invention.

EXPERIMENTS

Main Experiment

In the following experiments, weighed amount of distilled styrene (or hydrocarbon stream in gms) and weighed amount of additives (in ppm by weight of styrene or hydrocarbon stream) were taken in a tube reactor equipped with thermometer and nitrogen inlet and outlet. In these experiments, enough $N_2$ flow was maintained to ensure proper agitation. The reactions were carried out at 120° C. under continuous nitrogen flow for 2 hours. After the selected duration, the reactor was cooled to below 10° C. by immersing in crushed ice. The contents of the reactor were then poured in a beaker. To this same beaker, approximately for 1.5-2 g chilled polymerization mixture, about 80 g methanol was used to precipitate the polymer formed in the styrene solution. The precipitate obtained was filtered, dried to remove methanol, and weighed. The weight of the precipitate formed is reported as % polymer formed.

It may be noted that styrene was purified before use to remove the stabilizers.

In following examples, the prior additive is a composition consisting of aromatic compound and nitroxide compound, wherein aromatic compound is Quinine Methide (QM); and nitroxide compound is 1 oxyl-2,2,6,6, tetramethylpiperidin-4-ol (or 4 Hydroxy Tempo or 4-HT), which are taken in an amount of about 100, 150, 200, 300, or 400 ppm in various weight ratios of 90:10 [referred as QM:4HT (90:10)], 80:20 [referred as QM:4HT (80:20)], 70:30 [referred as QM:4HT (70:30)], 50:50 [referred as QM:4HT (50:50)], 30:70 [referred as QM:4HT (30:70)] and 20:80 [referred as QM:4HT (20:80)] of QM and 4-HT.

In following examples, the present additive composition is a composition comprising Quinine Methide (QM) being aromatic compound and 1 oxyl-2,2,6,6, tetramethylpiperidin-4-ol (or 4 Hydroxy Tempo or 4-HT) being nitroxide compound, and further comprising an amine selected from a group consisting of TIPA, Quadrol® and THEED, wherein about 1, 5, 10, 15, or 20 ppm of TIPA, Quadrol® or THEED is added to 100, 200, 300 or 400 ppm of the mixture of said QM and 4HT, and about 2 ppm of TIPA is added to 200 ppm of above-said mixture of QM and 4HT taken in above-said weight ratios of 90:10, 80:20, 70:30, 50:50, 30:70 and 20:80 of QM and 4-HT.

EXPERIMENTS

The results of above Main Experiment when performed with 10 g of distilled styrene by heating to 120° C. for 2 h are provided in Table-I, Table-II and Table-III.

TABLE I

| Weight Ratio of QM and 4HT in QM and 4HT mix. of Prior Art and Present Additives | % Polymer formed with Prior Art Additive (100 ppm of QM and 4HT mix.) | % Polymer formed with Present Additive (100 ppm of QM and 4HT mix., and 1 ppm of TIPA | Technical Effects of present composition |
|---|---|---|---|
| 90:10 | 3.13 | 1.30 | Polymerization inhibition efficiency of composition consisting of aromatic and nitroxide compounds (QM and 4HT) is substantially improved, and % polymer formed is substantially reduced on just on addition of 1 or 2 ppm of aliphatic tertiary amine in composition consisting of aromatic and nitroxide compounds (QM and 4HT). |
| 80:20 | 3.78 | 1.25 | |
| 50:50 | 4.95 | 0.98 | |
| 30:70 | 3.18 | 1.21 | |

TABLE II

| Weight Ratio of QM and 4HT in QM and 4HT mix. of Prior Art and Present Additives | % Polymer formed with Prior Art Additive (200 ppm of QM and 4HT mix.) | % Polymer formed with Present Additive (200 ppm of QM and 4HT mix., and 2 ppm of TIPA | Technical Effects of present composition |
|---|---|---|---|
| 90:10 | 1.64 | 0.23 | Polymerization inhibition efficiency of composition consisting of aromatic and nitroxide compounds (QM and 4HT) is substantially improved, and % polymer formed is substantially reduced on just on addition of 1 or 2 ppm of aliphatic tertiary amine in composition consisting of aromatic and nitroxide compounds (QM and 4HT). |
| 80:20 | 1.56 | 0.22 | |
| 50:50 | 1.93 | 0.11 | |
| 30:70 | 1.48 | 0.21 | |

The reasons for sudden increase in % polymer formed for prior art additive composition consisting of QM and 4-HT in weight ratio of 50:50, and for present additive composition comprising QM and 4-HT in weight ratio of 30:70 with TIPA are not known presently. However, it is understood from above Table-I and Table II that when just 1 ppm or 2 ppm of TIPA is added respectively to 100 ppm or 200 ppm of mixture of QM and 4-HT in various weight ratios (prior art additive), the efficiency of prior art additive to control and inhibit polymerization of styrene is, surprisingly and unexpectedly, improved substantially.

It can also be observed from Table-I and Table-II that polymerization of styrene is, surprisingly and unexpectedly, substantially reduced just on addition of 1 ppm or 2 ppm of TIPA respectively in 100 ppm or 200 ppm of the mixture of QM and 4-HT in various weight ratios (prior art additive).

It is also understood on comparing results of Table II with that of Table III that just by addition of 2 ppm of TIPA in 200 ppm of the mixture of QM and 4-HT in various weight ratios (prior art additive), the % polymer formed is either same or better than the prior art additive consisting of 400 ppm of the mixture of QM and 4-HT in various weight ratios which further confirms that just an addition of 2 ppm of TIPA in 200 ppm of prior art additive composition results in substantial saving of 200 ppm of prior art additive consisting of aromatic compound and nitroxide compound at various weight ratios.

In following examples, for above Main Experiment, the prior art additive composition and the present additive composition are taken in various weight ratios as indicated in the following Tables IV to X. The inventor has further compared the results of present compositions with additive composi-

TABLE III

| Weight Ratio of QM and 4HT in QM and 4HT mix. of Prior Art Additive | % Polymer formed with Prior Art Additive (150 ppm of QM and 4HT mix.) | % Polymer formed with Prior Art Additive (300 ppm of QM and 4HT mix.) | % Polymer formed with Prior Art Additive (400 ppm of QM and 4HT mix.) |
|---|---|---|---|
| 90:10 | 2.17 | 0.58 | 0.24 |
| 80:20 | 2.65 | 0.55 | 0.22 |
| 50:50 | 3.13 | 0.54 | 0.27 |
| 30:70 | 2.52 | 0.47 | 0.35 | tions comprising mixture of QM and 4HT, and above-described amines i) to ix), i.e. TBA, DBA, MEA, DEA, DPA, TEA, EDA, TEPA for comparative purposes. The results are given in Tables V to X.

In Table IV, the prior art additive composition consisting of mixture of QM+4HT in 100, 150, 200, 300 and 400 ppm dosages in % by wt. ratios of 90:10, 80:20, 70:30, 50:50, 30:70 and 20:80 of QM and 4HT is taken.

TABLE IV

| Active dosage (ppm) | QM:4HT (90:10) | QM:4HT (80:20) | QM:4HT (70:30) | QM:4HT (50:50) | QM:4HT (30:70) | QM:4HT (20:80) |
|---|---|---|---|---|---|---|
| 100 | 3.13 | 3.78 | 3.86 | 4.95 | 3.18 | 5.79 |
| 150 | 2.17 | 2.65 | 2.55 | 3.13 | 2.52 | 2.11 |
| 200 | 1.64 | 1.56 | 1.62 | 1.93 | 1.48 | 1.42 |
| 300 | 0.58 | 0.55 | 0.55 | 0.54 | 0.47 | 0.96 |
| 400 | 0.24 | 0.22 | 0.23 | 0.27 | 0.35 | 0.73 |

In Table V, the prior art additive composition consisting of mixture of QM+4HT in 100 ppm dosage in % by wt. ratios of 90:10, 80:20, 70:30, 50:50, 30:70 and 20:80 respectively of QM and 4HT, and comparative additive compositions comprising 100 ppm of mixture of QM and 4HT in % by wt. ratios of 90:10, 80:20, 70:30, 50:50, 30:70 and 20:80 respectively of QM and 4HT), and 5 ppm of comparative amine resulting in total dosage of 105 ppm of the composition are compared with present additive compositions comprising 100 ppm of mixture of QM and 4HT in % by wt. ratios of 90:10, 80:20, 70:30, 50:50, 30:70 and 20:80 respectively of QM and 4HT, and 5 ppm of present amine selected from TIPA, Quadrol® and THEED to result in total dosage of 105 ppm of the composition.

TABLE V

| Active Dosage (ppm) | QM:4HT (90:10) | QM:4HT (80:20) | QM:4HT (70:30) | QM:4HT (50:50) | QM:4HT (30:70) | QM:4HT (20:80) |
|---|---|---|---|---|---|---|
| 100 w/o amine | 3.13 | 3.78 | 3.86 | 4.95 | 3.18 | 5.79 |
| 100 + 5 (TIPA) | 1.05 | 0.95 | 1.21 | 0.98 | 1.05 | 1.2 |
| 100 + 5 (Quadrol) | 1.9 | 2.1 | 2.21 | 1.85 | 1.98 | 2.2 |
| 100 + 5 (THEED) | 1.75 | 1.80 | 1.95 | 1.7 | 1.65 | 2.0 |
| 100 + 5 (TBA) | 3.16 | 3.65 | 3.85 | 4.5 | 3.2 | 5.2 |
| 100 + 5 (DBA) | 3.22 | 3.79 | 3.95 | 4.91 | 3.29 | 5.8 |
| 100 + 5 (MEA) | 3.3 | 3.85 | 3.99 | 4.95 | 3.35 | 5.85 |
| 100 + 5 (DEA) | 3.2 | 3.8 | 3.86 | 5.1 | 3.2 | 5.75 |
| 100 + 5 (DPA) | 3.22 | 3.82 | 3.85 | 5.15 | 3.05 | 5.83 |
| 100 + 5 (TEA) | 3.31 | 3.75 | 3.98 | 5.05 | 3.3 | 5.89 |
| 100 + 5 (EDA) | 3.36 | 3.8 | 4.1 | 5.2 | 3.4 | 5.9 |
| 100 + 5 (TEPA) | 3.21 | 3.95 | 4.15 | 5.11 | 3.2 | 5.83 |

In Table VI, the above compositions of Table V are taken but with 10 ppm of comparative amine or present amine to result in total dosage of 110 ppm of the composition.

TABLE VI

| Active Dosage (ppm) | QM:4HT (90:10) | QM:4HT (80:20) | QM:4HT (70:30) | QM:4HT (50:50) | QM:4HT (30:70) | QM:4HT (20:80) |
|---|---|---|---|---|---|---|
| 100 w/o amine | 3.13 | 3.78 | 3.86 | 4.95 | 3.18 | 5.79 |
| 100 + 10 (TIPA) | 0.95 | 0.85 | 1.05 | 1.05 | 0.9 | 1.05 |
| 100 + 10 (Quadrol) | 1.78 | 1.90 | 2.0 | 1.95 | 1.72 | 2.15 |
| 100 + 10 (THEED) | 1.65 | 1.65 | 1.75 | 1.75 | 1.55 | 1.9 |
| 100 + 10 (TBA) | 3.2 | 3.69 | 3.92 | 4.65 | 3.35 | 5.3 |
| 100 + 10 (DBA) | 3.3 | 3.82 | 4.1 | 5.1 | 3.2 | 6.0 |
| 100 + 10 (MEA) | 3.35 | 3.8 | 4.0 | 5.11 | 3.45 | 6.1 |
| 100 + 10 (DEA) | 3.39 | 3.91 | 4.05 | 5.23 | 3.15 | 6.38 |
| 100 + 10 (DPA) | 3.3 | 3.75 | 3.91 | 5.16 | 3.0 | 5.95 |
| 100 + 10 (TEA) | 3.45 | 3.85 | 4.0 | 5.05 | 3.25 | 6.0 |
| 100 + 10 (EDA) | 3.51 | 3.92 | 4.15 | 5.11 | 3.29 | 6.25 |
| 100 + 10 (TEPA) | 3.35 | 3.95 | 4.2 | 5.21 | 3.3 | 6.2 |

In Table VII, the above compositions of Table V are taken but with 20 ppm of comparative amine or present amine to result in total dosage of 120 ppm of the composition.

TABLE VII

| Active Dosage (ppm) | QM:4HT (90:10) | QM:4HT (80:20) | QM:4HT (70:30) | QM:4HT (50:50) | QM:4HT (30:70) | QM:4HT (20:80) |
|---|---|---|---|---|---|---|
| 100 w/o amine | 3.13 | 3.78 | 3.86 | 4.95 | 3.18 | 5.79 |
| 100 + 20 (TIPA) | 1.10 | 0.95 | 1.15 | 1.15 | 1.02 | 1.15 |
| 100 + 20 (Quadrol) | 1.90 | 1.99 | 2.1 | 2.1 | 1.85 | 2.24 |
| 100 + 20 (THEED) | 1.85 | 1.75 | 1.86 | 1.85 | 1.60 | 2.01 |
| 100 + 20 (TBA) | 3.25 | 3.85 | 4.0 | 4.78 | 3.45 | 5.47 |
| 100 + 20 (DBA) | 3.32 | 3.96 | 4.05 | 4.95 | 3.41 | 6.23 |
| 100 + 20 (MEA) | 3.2 | 3.83 | 4.1 | 5.1 | 3.55 | 6.28 |
| 100 + 20 (DEA) | 3.29 | 3.78 | 4.15 | 5.15 | 3.21 | 6.45 |
| 100 + 20 (DPA) | 3.4 | 3.89 | 4.08 | 5.2 | 3.24 | 6.05 |
| 100 + 20 (TEA) | 3.35 | 3.99 | 4.15 | 5.23 | 3.35 | 6.14 |
| 100 + 20 (EDA) | 3.45 | 4.05 | 4.2 | 5.21 | 3.39 | 6.35 |
| 100 + 20 (TEPA) | 3.5 | 4.1 | 4.1 | 5.36 | 3.45 | 6.4 |

In Table VIII, the prior art additive composition consisting of mixture of QM+4HT in 200, 300 and 400 ppm dosage in % by wt. ratio of 90:10 respectively of QM and 4HT, and comparative additive compositions comprising 200, 300 and 400 ppm of mixture of QM and 4HT in % by wt. ratio of 90:10 respectively of QM and 4HT, and 10, 15 and 20 ppm of comparative amine resulting in total dosage of 210, 315 and 420 ppm of the composition are compared with present additive compositions comprising 200, 300 and 400 ppm of mixture of QM and 4HT in % by wt. ratio of 90:10 respectively of QM and 4HT, and 10, 15 and 20 ppm of present amine selected from TIPA, Quadrol® and THEED to result in total dosage of 210, 315 and 420 ppm of the composition.

All of above experiments confirm that only the present additive compositions comprising mixture of QM and 4HT and tertiary amine selected from a group comprising TIPA, Quadrol® and THEED result in improvement of polymerization inhibition efficiency of the prior art additives.

The above findings confirm that present composition is more economical and environment friendly than prior art composition consisting of mixture of aromatic and nitroxide compounds.

The above findings also confirm synergistic, surprising and unexpected effects of present composition.

TABLE VIII

| Dosage, Active (ppm) | QM:4HT (90:10) | TIPA | Quadrol | THEED | TBA | DBA | MEA | DEA | DPA | TEA | EDA | TEPA |
|---|---|---|---|---|---|---|---|---|---|---|---|---|
| 200 + 10 | 1.64 | 0.30 | 0.45 | 0.40 | 1.69 | 1.70 | 1.72 | 1.64 | 1.66 | 1.75 | 1.68 | 1.76 |
| 300 + 15 | 0.58 | 0.05 | 0.15 | 0.11 | 0.62 | 0.66 | 0.65 | 0.60 | 0.63 | 0.67 | 0.72 | 0.74 |
| 400 + 20 | 0.24 | 0 | 0 | 0 | 0.33 | 0.32 | 0.37 | 0.29 | 0.30 | 0.32 | 0.35 | 0.40 |

In Table IX, the above compositions of Table VIII are taken but with % by wt. ratio of 80:20 of QM and 4HT.

Above experimental results also confirm that presently provided composition is far superior than prior art additive

TABLE IX

| Dosage, Active (ppm) | QM:4HT (80:20) | TIPA | Quadrol ® | THEED | TBA | DBA | MEA | DEA | DPA | TEA | EDA | TEPA |
|---|---|---|---|---|---|---|---|---|---|---|---|---|
| 200 + 10 | 1.56 | 0.22 | 0.40 | 0.38 | 1.68 | 1.68 | 1.68 | 1.73 | 1.75 | 1.70 | 1.76 | 1.69 |
| 300 + 15 | 0.55 | 0 | 0.07 | 0.06 | 0.66 | 0.7 | 0.72 | 0.66 | 0.69 | 0.70 | 0.75 | 0.80 |
| 400 + 20 | 0.22 | 0 | 0 | 0 | 0.25 | 0.30 | 0.24 | 0.27 | 0.3 | 0.35 | 0.36 | 0.40 |

In Table X, the above compositions of Table VIII are taken but with 50 ppm of the present amine or comparative amine resulting in 150, 250 and 350 ppm of the composition.

composition, and hence, has technical advantages and surprising effects over the prior art additive.

The invention claimed is:

1. An improved amine based additive composition for controlling and inhibition of polymerization of aromatic vinyl monomers including styrene comprising:
(A) one or more of the quinone methide or derivatives thereof,
(B) one or more of nitroxides (i.e. nitroxyl) compounds, and
characterized in that the said composition further comprises:

TABLE X

| Dosage, Active (ppm) | QM:4HT (90:10) | TIPA | Quadrol ® | THEED | MEA | DPA |
|---|---|---|---|---|---|---|
| 100 + 50 | 3.13 | 1.25 | 2.20 | 1.95 | 3.65 | 3.70 |
| 200 + 50 | 1.64 | 0.50 | 0.70 | 0.65 | 1.90 | 1.85 |
| 300 + 50 | 0.58 | 0.12 | 0.30 | 0.28 | 0.90 | 0.87 |

(C) one or more of aliphatic tertiary amines or mixture thereof.

2. The composition as claimed in claim 1, wherein said aliphatic tertiary amine contains hydroxyl groups in alkyl chain of the tertiary amine, and wherein number of the hydroxyl groups in the alkyl chain of the tertiary amine is selected from the group comprising one or more, and three or four hydroxyl groups in the alkyl chain of the tertiary amine.

3. The composition as claimed in claim 1, wherein said aliphatic tertiary amine is tri-isopropanol amine or tris(2-hydroxypropyl)amine [TIPA].

4. The composition as claimed in claim 1, wherein said aliphatic tertiary amine is N,N,N',N'-Tetrakis(2-hydroxyethyl)ethylene-diamine) (THEED).

5. The composition as claimed in claim 1, wherein said aliphatic tertiary amine is N,N,N',N'-Tetrakis(2-hydroxypropyl)ethylene-diamine) (Quadrol®).

6. The composition as claimed in claim 1, wherein said aliphatic tertiary amine comprises one or more of TIPA, THEED and Quadrol®.

7. An improved amine based additive composition for controlling and inhibition of polymerization of aromatic vinyl monomers including styrene comprising:
(A) one or more of the quinone methide or derivatives thereof,
(B) one or more of nitroxides (i.e. nitroxyl) compounds, and
characterized in that the said composition further comprises:
(C) one or more of tertiary amines,
wherein said tertiary amine is selected from a group consisting of:
i) hydroxyl alkyl tertiary amine which is tris(2-hydroxypropyl)amine (TIPA);
ii) propylene oxide treated amine which is N,N,N',N'-Tetrakis(2-hydroxypropyl)ethylene-diamine) (Quadrol®); and
iii) ethylene oxide treated amine which is N,N,N',N'-Tetrakis(2-hydroxyethyl)ethylene-diamine) (THEED); or
iv) mixture thereof.

8. The composition as claimed in claim 1, wherein said composition comprises:
a) 40 to 99.9% by weight of I) mixture of one or more of said quinone methide or derivatives thereof and one or more of said nitroxides (i.e. nitroxyl) compounds; and
b) 0.1 to 60% by weight of II) one or more of said tertiary amines or mixture thereof.

9. The composition as claimed in claim 1, wherein said quinone methide or derivatives thereof (QM) includes benzyl quinone methide.

10. The composition as claimed in claim 1, wherein said nitroxides (i.e. nitroxyl) compounds include 1 oxyl-2,2,6,6, tetramethylpiperidin-4-ol (or 4 Hydroxy Tempo or 4HT).

11. The composition as claimed in claim 1, wherein said mixture of QM and 4HT comprises QM in an amount varying from 0.5 to 99.5% by wt. and 4HT in an amount varying from 99.5 to 0.5% by wt. of the said mixture.

12. The composition as claimed in claim 1, wherein said mixture of QM and 4HT comprises QM and 4HT in a weight ratio selected from the group comprising varying from 99.5: 0.5 to 0.5:99.5, from 95:5 to 5:95, and from 90:10 to 10:90.

13. The composition as claimed in claim 1, wherein said tertiary amine or mixture thereof is taken an amount varying from 0.01 to 60% by wt. of the composition.

14. The composition as claimed in claim 1, wherein said composition does not comprise:
i) triethanolamine (TEA);
ii) Tris[N-butylamine] (TBA);
iii) monoethanolamine (MEA);
iv) dibutyl amine (DBA);
v) diethanol amine (DEA);
vi) dipropyl amine (DPA);
vii) ethylene diamine (EDA); and
viii) tetraethylenepentamine (TEPA), and
ix) mixture thereof.

15. The composition as claimed in claim 1, wherein said composition is added to the stream containing aromatic vinyl monomers including styrene in an amount selected from the group comprising varying from 0.01 ppm to 2000 ppm, and from 1 ppm to 2000 ppm by weight of the stream of the monomers including styrene.

16. A method of using said amine based additive composition of claim 1 for controlling and inhibition of polymerization of aromatic vinyl monomers including styrene, wherein the stream comprising aromatic vinyl monomers including styrene is treated with said additive composition comprising:
(A) one or more of said quinone methide or derivatives thereof,
(B) one or more of said nitroxides (i.e. nitroxyl) compounds, and
characterized in that the said composition further comprises:
(C) one or more of said aliphatic tertiary amines or mixture thereof.

17. The method as claimed in claim 16, wherein said stream comprising aromatic vinyl monomers including styrene is treated with an amount of said additive composition selected from the group comprising varying from 0.01 ppm to 2000 ppm, and from 1 ppm to 2000 ppm based on weight of the monomers.

18. The method as claimed in claim 16, wherein said quinone methide or derivatives thereof, said nitroxides (i.e. nitroxyl) compounds, and said tertiary amines are added to the monomers stream either individually or after mixing.

19. A method for controlling and inhibiting polymerization of aromatic vinyl monomers including styrene by adding said amine based additive composition of claim 1 to the stream comprising aromatic vinyl monomers including styrene, wherein the additive composition comprises:
(A) one or more of said quinone methide or derivatives thereof,
(B) one or more of said nitroxides (i.e. nitroxyl) compounds, and
characterized in that the said composition further comprises:
(C) one or more of said aliphatic tertiary amines or mixture thereof.

20. The method as claimed in claim 19, wherein said additive composition is added in an amount selected from the group comprising varying from 0.01 ppm to 2000 ppm, and from 1 ppm to 2000 ppm to the aromatic vinyl monomers stream including styrene based on weight of the monomers.

21. The method as claimed in claim 19, wherein said quinone methide or derivatives thereof, said nitroxides (i.e. nitroxyl) compounds, and said tertiary amines are added to the monomers stream either individually or after mixing.

22. The method as claimed in claim 16, wherein said composition is used over a range of temperature varying from 50 degree C. to 180 degree C.

23. A method for preparing additive composition as claimed in claim 1 for controlling and inhibiting polymerization of aromatic vinyl monomers including styrene, wherein the method comprises step of mixing:
(A) one or more of said quinone methide or derivatives thereof, and (B) one or more of said nitroxides (i.e. nitroxyl) compounds, and characterized in that said quinone methide or derivatives thereof and said nitroxides (i.e. nitroxyl) compounds or mixture thereof is further mixed with (C) one or more of said tertiary amines.

24. The composition as claimed in claim 1, wherein said quinone methide or derivatives thereof (QM) is 4-benzylidene, 2,6-di-tert-butyl cyclohexa-2,5-dienone.

25. The method as claimed in claim 19, wherein said composition is used over a range of temperature varying from 50 degree C. to 180 degree C.

* * * * *